United States Patent
Reinschke et al.

(10) Patent No.: US 8,597,176 B2
(45) Date of Patent: Dec. 3, 2013

(54) ENDOSCOPIC CAPSULE

(75) Inventors: Johannes Reinschke, Nürnberg (DE); Günter Ries, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1074 days.

(21) Appl. No.: 12/297,719

(22) PCT Filed: Mar. 6, 2007

(86) PCT No.: PCT/EP2007/052064
§ 371 (c)(1), (2), (4) Date: Oct. 20, 2008

(87) PCT Pub. No.: WO2007/124970
PCT Pub. Date: Nov. 8, 2007

(65) Prior Publication Data
US 2009/0105541 A1  Apr. 23, 2009

(30) Foreign Application Priority Data
Apr. 26, 2006  (DE) .......................... 10 2006 019 987

(51) Int. Cl.
*A61B 1/00* (2006.01)
*A61B 1/04* (2006.01)

(52) U.S. Cl.
USPC ......................................... 600/117; 600/109

(58) Field of Classification Search
USPC ................... 600/109, 160, 424, 130, 407
See application file for complete search history.

(56) References Cited

U.S. PATENT DOCUMENTS

| 4,278,077 | A | 7/1981 | Mizumoto | |
|---|---|---|---|---|
| 6,233,476 | B1 * | 5/2001 | Strommer et al. | 600/424 |
| 7,354,398 | B2 * | 4/2008 | Kanazawa | 600/109 |
| 7,604,591 | B2 * | 10/2009 | Uchiyama et al. | 600/130 |
| 7,924,000 | B2 * | 4/2011 | Susel et al. | 324/261 |
| 2002/0165592 | A1 | 11/2002 | Glukhovsky et al. | |
| 2003/0060702 | A1 | 3/2003 | Kuth et al. | |
| 2003/0216639 | A1 * | 11/2003 | Gilboa et al. | 600/424 |
| 2004/0138552 | A1 * | 7/2004 | Harel et al. | 600/407 |
| 2004/0176669 | A1 * | 9/2004 | Colvin, Jr. | 600/316 |
| 2005/0029437 | A1 * | 2/2005 | Hasegawa et al. | 250/226 |
| 2005/0062562 | A1 * | 3/2005 | Ries | 335/1 |
| 2005/0154294 | A1 | 7/2005 | Uchiyama et al. | |

(Continued)

FOREIGN PATENT DOCUMENTS

DE  1020044052614  1/2000

*Primary Examiner* — Philip R Smith
*Assistant Examiner* — William Chou
(74) *Attorney, Agent, or Firm* — Schiff Hardin LLP

(57) ABSTRACT

An endoscopy capsule contains an induction coil that is elongated along a longitudinal axis thereof, the endoscopy coil supplying power to components within the endoscopy capsule. A magnetic element in the endoscopy capsule has a magnetic dipole moment and interacts with an external magnetic field to navigate the endoscopy capsule within the body of a subject. The magnetic element is oriented so that the magnetic dipole element is aligned perpendicularly to the longitudinal axis of the induction coil. The endoscopy capsule has a cross-sectional area, in a plane having a normal aligned in the direction of the longitudinal axis of the induction coil, which contains both a cross-section through the magnetic element and a cross-section through the induction coil. The magnetic element has a length along the longitudinal axis of the induction coil so that the magnetic element projects beyond the induction coil at each end thereof.

7 Claims, 2 Drawing Sheets

(56) References Cited

U.S. PATENT DOCUMENTS

| | | |
|---|---|---|
| 2005/0216231 A1* | 9/2005 | Aoki et al. .................... 702/183 |
| 2005/0228259 A1 | 10/2005 | Glukhovsky et al. |
| 2006/0152309 A1* | 7/2006 | Mintchev et al. ............... 335/58 |
| 2006/0169293 A1 | 8/2006 | Yokoi et al. |
| 2007/0244388 A1* | 10/2007 | Sato et al. ..................... 600/424 |
| 2008/0139883 A1 | 6/2008 | Uchiyama |
| 2008/0281188 A1* | 11/2008 | Aoki et al. .................... 600/424 |
| 2009/0048484 A1* | 2/2009 | Swain et al. ................... 600/118 |

* cited by examiner

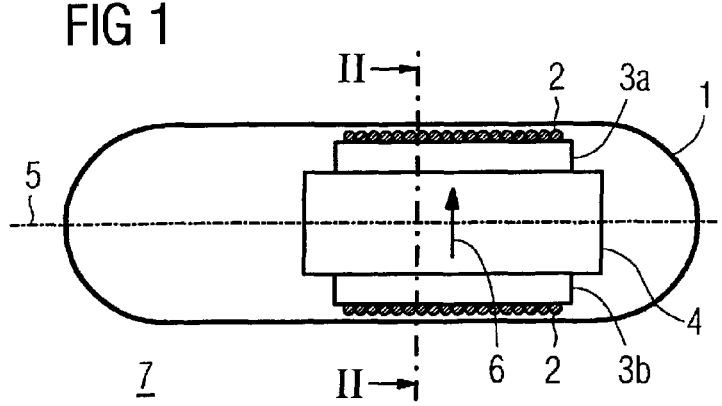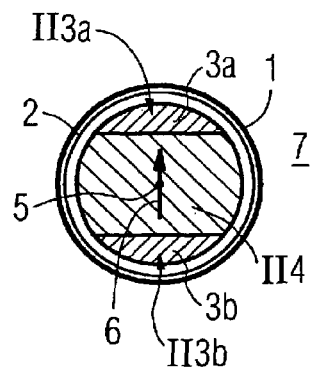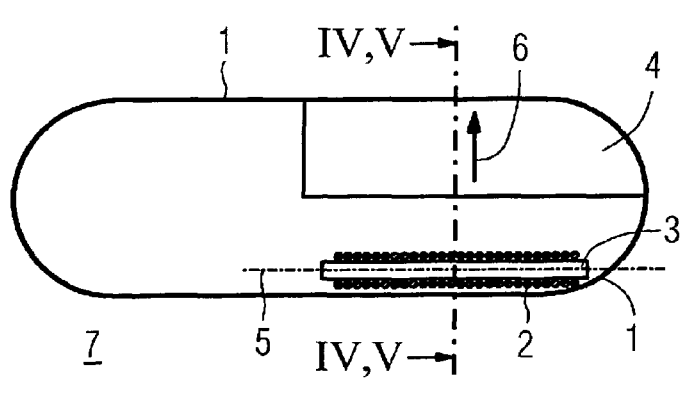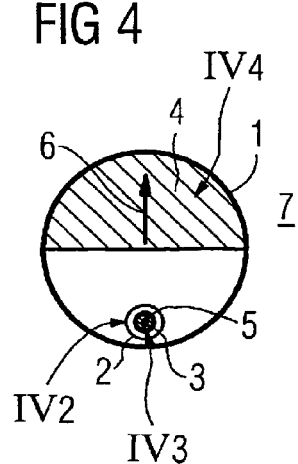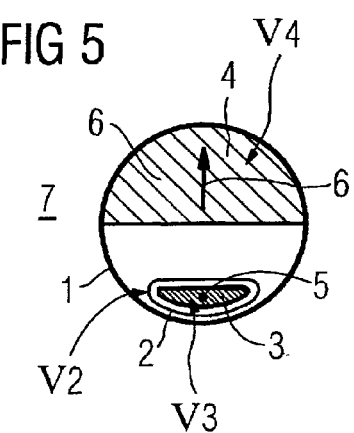

ENDOSCOPIC CAPSULE

BACKGROUND OF THE INVENTION

1. Field of the Invention

The present invention concerns an endoscopy capsule of the type that is magnetically navigable inside a patient, in particular his gastrointestinal tract. The endoscopy capsule (designed with an induction coil) has a magnetic dipole element for the navigation, which interacts with a magnetic field that is generated by a coil system at least partially surrounding the body of the patient. As used herein, navigation of the endoscopy capsule is both the translational movement as well as rotation and tilting of the capsule.

2. Description of the Prior Art

Minimally-invasive and non-invasive medical techniques are used and developed ever more frequently for examination and treatment of a person or animal as a patient. The use of endoscopes which are introduced into the patient via body orifices or small incisions has been typical for a long time. Inspection or manipulation devices (for example a camera or a grabber) to execute a desired action are located at the tip of a more or less long, flexible catheter. These can be used only to a limited extent due to friction effects and the limited length and flexibility of endoscopes.

A wirelessly operating device for endoscopy is known from DE 101 42 253. A device known as an "endorobot" in the form of an endoscopy capsule of approximately 2 cm length and approximately 1 cm diameter contains an inspection, diagnosis or therapy device. For example, this can be a video camera, a biopsy probe, a clip or a medicine reservoir. The capsule contains a magnetic element with a magnetic dipole moment, for example a permanent magnet. The capsule is moved wirelessly in the patient. For this purpose, the patient lies entirely or partially in an electrical coil system composed of multiple (for example fourteen) individual coils. Suitable gradient magnetic fields and magnetic fields, which generate corresponding forces for a translational movement and rotation moments for a rotation and tilt movement at the capsule located in the patient, are generated by the coil system in order to navigate the capsule in the patient in this manner. Since the rotation moments and forces acting on the capsule result from the product of the magnetic dipole moment and the magnetic field strength, namely the magnetic field gradient at the location of the capsule, it is advantageous to integrate as large a magnetic element as possible into the capsule in order to obtain sufficiently high rotation moments or forces. As an alternative, the magnetic field or the magnetic field gradient would have to be increased. However, this leads to very high power consumption and accompanying losses in the coil system since the ohmic power loss increases with the square of the magnetic field or magnetic field gradients to be generated.

In addition to a magnetic element with magnetic dipole moment, such an endoscopy capsule normally contains electrically conductive and/or ferromagnetic objects such as, for example, a battery or an induction coil with a ferrite core. With given external dimensions of the endoscopy capsule, the arrangement of the cited parts in the endoscopy capsule must be selected as advantageously as possible so that the electrically conductive and/or ferromagnetic objects in the endoscopy capsule do not attenuate the magnetic dipole field relevant for the magnetic navigation. Moreover, it is desirable that the magnetic element does not interfere with the adjacent objects or even impairs their function.

SUMMARY OF THE INVENTION

An object of the present invention is to provide an improved endoscopy capsule in which the induction coil and the magnetic element largely do not mutually affect one another.

The above object is achieved in accordance with the present invention by an endoscopy capsule having an induction coil that is elongated along a longitudinal axis thereof, and that supplies power to components within the endoscopy capsule, and having a magnetic element exhibiting a magnetic dipole moment that interacts with an externally applied magnetic field in order to navigate the endoscopy capsule. The magnetic dipole moment is aligned perpendicularly to the longitudinal axis of the induction coil, and a cross-sectional area of the endoscopy capsule, having a normal aligned in the direction of the longitudinal axis of the induction coil, contains both a cross-section through the magnetic element and a cross-section through the induction coil. The magnetic element is dimensioned in both directions of the longitudinal induction coil axis so as to project beyond the induction coil.

Magnetic field components running parallel to the coil longitudinal axis are largely avoided by means of this arrangement of the magnetic element relative to the induction coil provided to supply power to the endoscopy capsule. The inductive energy transfer from the outside to the induction coil by means of an alternating magnetic field thus proceeds unaffected by the magnetic dipole moment of the magnetic element.

It is thus advantageous for the magnetic element to be at least partially enclosed by the induction coil.

It can also be advantageous for the magnetic element to be arranged outside of the induction coil.

The endoscopy capsule also has an external wall in which at least a portion of the induction coil is integrated.

The endoscopy capsule advantageously has an external wall in which at least a portion of the magnetic element is integrated.

The induction coil is advantageously provided with at least one weakly magnetic core. Since a weakly magnetic core (in particular a ferrite core) acts in an induction-amplifying manner, a more effective energy transfer to the induction coil can be achieved.

It is thereby advantageous for the at least one weakly-magnetic core to be executed positively at least in part with the induction coil.

It is advantageous for the at least one weakly-magnetic core to have a circular cross-section or a cross-section that is shaped like a circular segment.

It is also advantageous for the magnetic element to be fixed with the induction coil and/or the at least one weakly-magnetic core.

It is advantageous for the at least one weakly-magnetic core to be executed from weakly-magnetic ferrite.

BRIEF DESCRIPTION OF THE DRAWINGS

FIG. 1 shows a longitudinal section of an endoscopy capsule in accordance with the present invention, having a magnetic element arranged in an induction coil provided with a weakly-magnetic core.

FIG. 2 shows the endoscopy capsule of FIG. 1 in cross-section.

FIG. 3 shows an endoscopy capsule in a longitudinal section, having a magnetic element arranged next to an induction coil provided with a weakly-magnetic core.

FIG. 4 shows the endoscopy capsule of FIG. 3 in cross-section, in an embodiment wherein the induction coil and the weakly-magnetic coil have a circular cross-section.

FIG. 5 shows the endoscopy capsule of FIG. 3 in cross-section, in an embodiment wherein the induction coil and the weakly-magnetic core have a cross-section formed as a circular segment.

DESCRIPTION OF THE PREFERRED EMBODIMENTS

Figure 6:
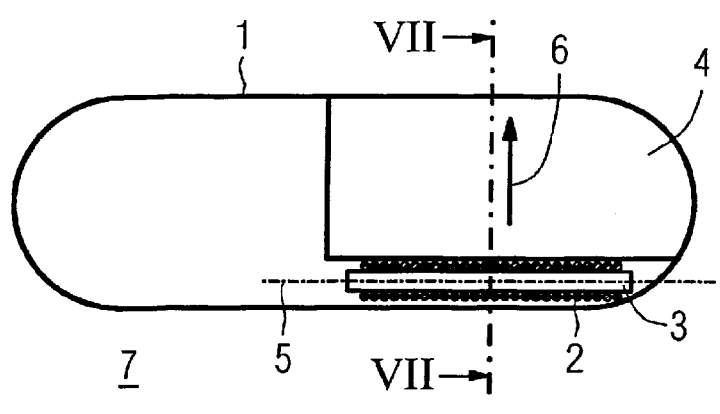
FIG. 6 shows an endoscopy capsule in longitudinal section, having a magnetic element rigidly mounted next to an induction coil provided with a weakly-magnetic core.

Exemplary embodiments of the endoscopy capsule 7 according to the invention are respectively presented in longitudinal section in FIGS. 1, 3 and 6. An induction coil 2 with a weakly-magnetic core 3 (FIGS. 3 and 6) or with two weakly-magnetic cores 3a, 3b (FIG. 1) and a magnetic element 4 with a magnetic dipole moment 6 (in particular a permanent magnet) are arranged within the endoscopy capsule 7 which—for example—has an oblong, rotationally-symmetrical, cigar-shaped external wall 1. In particular, a ferrite core is provided as a weakly-magnetic core 3, 3a, 3b. The magnetic dipole moment 6 of the magnetic element 4 is respectively arranged perpendicular to the longitudinal axis 5 of the induction coil 2. The magnetic field forming the basis of the magnetic dipole moment 6 is thus aligned nearly perpendicular to the longitudinal axis 5 of the coil in the entire region of the induction coil 2 and associated weakly-magnetic core 3, 3a, 3b. For clarity, additional objects that are provided and likewise integrated into the endoscopy capsule 7 (for example for inspection, therapy or diagnosis) are not shown in FIGS. 1, 3 and 6. The induction coil 2 serves to supply power to the endoscopy capsule 7. An alternating magnetic field is thereby generated at the location of the endoscopy capsule 7 by a coil system (arranged outside of said endoscopy capsule 7; not shown) which induces an induction voltage in the induction coil 2. This induction voltage is directly used to operate the individual objects to be supplied with electrical energy, or can also be cached in a buffer (not shown in Figures) likewise arranged in the endoscopy capsule 7. The induction coil 2 with or without buffer (i.e. energy cache) is a part of a power supply unit that is not explicitly shown. The one (FIGS. 3 and 6), the two (FIG. 1) or multiple weakly-magnetic cores 3, 3a, 3b are provided in an induction-amplifying manner inside the corresponding induction coil 2 for more effective energy transfer.

According to the exemplary embodiment in FIG. 1, the magnetic element 4 is arranged along the longitudinal axis 5 of the induction coil 2 so that the longitudinal axis 5 of the coil 2 coincides with the longitudinal axis of the magnetic element 4. The induction coil 2 with its two weakly-magnetic cores 3a, 3b comprises the magnetic element 4, such that the magnetic element 4 extends beyond the induction coil 2 with the weakly-magnetic cores 3a, 3b in both directions of the longitudinal induction coil axis 5.

A circular cross-section 11 of the endoscopy capsule 7 according to FIG. 1 is presented in FIG. 2, the surface normal of which is aligned in the direction of the longitudinal induction coil axis 5. The cross-section II a cross-section II2 through the induction coil 2 provided with two weakly-magnetic cores 3a, 3b and a cross-section II4 through the magnetic element 4. The cross-section II2 of the induction coil 2 is likewise circular, since this is executed positively with the wall 1 of the endoscopy capsule 7. The cross-sections II3a, II3b of the two weakly-magnetic elements 3a, 3b are contrarily shaped like circle segments (i.e. crescent-shaped) and are executed positively with the induction coil 2 only on one side. Between the two weakly-magnetic cores 3a, 3b, the magnetic element 4 is likewise arranged positively with the induction coil 2.

According to the exemplary embodiment in FIG. 3, the magnetic element 4 is arranged separate from and adjacent to the induction coil 2 provided with a weakly-magnetic core 3. Here as well, the magnetic element 4 extends beyond the induction coil 2 with its weakly-magnetic core 3 in both directions of the longitudinal induction coil axis 5. The space generated with the separation between magnetic element 4 and induction coil 2 can be used for integrated inspection, diagnosis or therapy objects (not shown), for example.

A circular cross-section IV of the endoscopy capsule 7 according to FIG. 3 is shown in FIG. 4, the surface normal of which is aligned in the direction of the longitudinal induction coil axis 5. The cross-section 4 has a cross-section IV2 through the induction coil 2 provided with the weakly-magnetic core 3 and a cross-section IV4 through the magnetic element 4. The cross-section IV4 of the magnetic element 4 is shaped like a circular segment here and is executed positively in part with the capsule wall 1. The induction coil 2 is arranged separate from the magnetic element 4 on the opposite side of the capsule cross-section IV, near the wall 1. The cross-section IV2 of the induction coil 2 and also the cross-section IV3 of the weakly-magnetic core 5 (executed positively with the induction coil 2) are designed circular in shape.

A circular cross-section V of the endoscopy capsule 7 according to FIG. 3 is presented in an additional exemplary embodiment in FIG. 5, the surface normal of which is aligned in the direction of the longitudinal induction coil axis 5. The cross-section 5 thereby likewise comprises a cross-section V2 through the induction coil 2 provided with a weakly-magnetic core 3 and a cross-section V4 through the magnetic element 4. Here as well, the cross-section V4 of the magnetic element 4 is shaped like a circular segment and is executed positively in part with the capsule wall 1. The induction coil 2 provided with the weakly-magnetic core 3 is arranged separate from the magnetic element 4 on the opposite side of the capsule cross-section V, positive with the capsule wall 1. The cross-section V2 of the induction coil 2 and also the cross-section V3 of the weakly-magnetic core 5 (executed positively with the induction coil 2) are hereby designed shaped like circular segments.

According to the exemplary embodiment in FIG. 6, the magnetic element is arranged positively and adjacent to an induction coil 2 provided with a weakly-magnetic core 3. Here as well, the magnetic element 4 protrudes beyond the induction coil 2 with its weakly-magnetic core 3 in both directions of the longitudinal induction coil axis 5.

Figure 7:
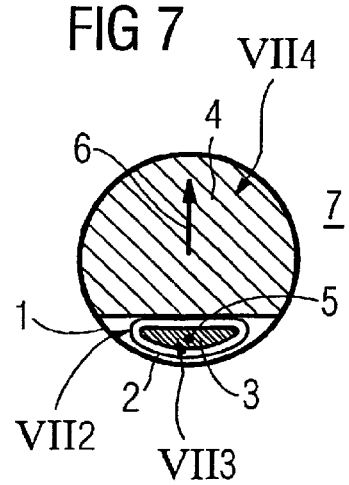
FIG. 7 shows the endoscopy capsule of FIG. 6 in cross-section, in an embodiment wherein the induction coil and the weakly-magnetic coil have a circular cross-section.

A circular cross-section VII of the endoscopy capsule 7 according to FIG. 6 is presented in FIG. 7, the surface normal of which is aligned in the direction of the longitudinal induction coil axis 5. Here as well, the cross-section VII comprises a cross-section VII2 through the induction coil 2 provided with a weakly-magnetic core 3 and a cross-section VII4 through the magnetic element 4. The cross-section VII4 of the magnetic element 4 is circular and executed positively in part with the capsule wall 1 and the induction coil 2. The induction coil 2 is arranged positively with the capsule wall 1, adjacent to the magnetic element 4 and on the opposite side of the capsule cross-section VII. The cross-section VII2 of the induction coil 2 and also the cross-section VII3 of the weakly-magnetic core 3 executed positively with the induction coil 2 are designed in the same of circular segments.

The capsule 7 to be taken orally in particular has a diameter in the range from 10 to 14 mm and a length in the range from 10 to 30 mm. If the capsule 7 should only be inserted rectally, it can also possess a diameter in the range from 10 to 30 mm with a length in the range from 10 to 50 mm.

Although modifications and changes may be suggested by those skilled in the art, it is the intention of the inventors to embody within the patent warranted heron all changes and modifications as reasonably and properly come within the scope of their contribution to the art.

We claim as our invention:

1. An endoscopy capsule comprising:

a capsule housing configured for in vivo movement in a patient, said capsule housing containing at least one power-consuming component;

an induction coil in said housing configured to interact with an extracorporeally-applied alternating magnetic field in order to effect power transfer from said alternating magnetic field to said induction coil in order to supply power to said at least one power-consuming component from said induction coil, said induction coil being elongated along a longitudinal axis thereof;

a permanently magnetic element rigidly connected to said capsule housing and at least partially enclosed by said induction coil, said permanently magnetic element exhibiting a magnetic dipole moment produced by the permanently magnetic element itself and interacting with an extracorporeally-applied navigation magnetic field in order to navigate said movement of the endoscopy capsule housing in vivo;

said permanently magnetic element being oriented relative to said capsule housing to align said magnetic dipole moment perpendicularly to said longitudinal axis of said induction coil;

said capsule housing having a cross-sectional area, with a normal thereto oriented in a direction of said longitudinal axis, said cross-sectional area comprising both a cross-section through said permanently magnetic element and a cross-section through said induction coil; and said permanently magnetic element having dimensions along opposite directions of said longitudinal axis of said induction coil to cause said permanently magnetic element to project beyond said induction coil in both said directions, said projection beyond said induction coil in both said directions making said power transfer substantially unaffected by said magnetic dipole moment of said permanently magnetic element.

2. An endoscopy capsule as claimed in claim 1 wherein said induction coil comprises at least one weakly-magnetic core element.

3. An endoscopy capsule as claimed in claim 2 wherein at least a portion of said weakly-magnetic core element is rigidly attached to said induction coil.

4. An endoscopy capsule as claimed in claim 2 wherein said weakly-magnetic core element has a cross-section with a shape selected from the group consisting of a circle and a circular segment.

5. An endoscopy capsule as claimed in claim 2 wherein said permanently magnetic element is rigidly attached to said weakly-magnetic core element.

6. An endoscopy capsule as claimed in claim 2 wherein said weakly-magnetic core element is comprised of weakly-magnetic ferrite.

7. An endoscopy capsule as claimed in claim 1 wherein said permanently magnetic element is rigidly attached to said induction coil.

* * * * *